(12) United States Patent
Pierik et al.

(10) Patent No.: US 9,616,661 B2
(45) Date of Patent: Apr. 11, 2017

(54) INKJET DEVICE AND METHOD FOR THE CONTROLLED POSITIONING OF DROPLETS OF A SUBSTANCE ONTO A SUBSTRATE

(75) Inventors: Anke Pierik, Eindhoven (NL); Antonius Johannes Jo Wismans, Eindhoven (NL); Willem-Jan A. De Wijs, Eindhoven (NL); Johan Frederik Dijksman, Eindhoven (NL); Martin Maurice Vernhout, Eindhoven (NL); Adrianus Theodorus Anthonius Maria Raaijmakers, Eindhoven (NL); Leonardus Johannes Cornelius Van Den Besselaar, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1886 days.

(21) Appl. No.: 12/089,449

(22) PCT Filed: Oct. 3, 2006

(86) PCT No.: PCT/IB2006/053602
§ 371 (c)(1),
(2), (4) Date: Apr. 7, 2008

(87) PCT Pub. No.: WO2007/042966
PCT Pub. Date: Apr. 19, 2007

(65) Prior Publication Data
US 2008/0211849 A1    Sep. 4, 2008

(30) Foreign Application Priority Data
Oct. 7, 2005  (EP) .................................. 05109346

(51) Int. Cl.
*B41J 29/38*    (2006.01)
*B41J 2/04*     (2006.01)
(Continued)

(52) U.S. Cl.
CPC ......... *B41J 2/04586* (2013.01); *B01L 3/0268* (2013.01); *B41J 2/0456* (2013.01);
(Continued)

(58) Field of Classification Search
USPC ......................................... 347/12, 14, 19, 40
See application file for complete search history.

(56) References Cited

U.S. PATENT DOCUMENTS 6,224,180 B1 * 5/2001 Pham-Van-Diep et al. ...... 347/2
6,575,550 B1   6/2003 Steinfield
(Continued)

FOREIGN PATENT DOCUMENTS

EP    1179368 A2    2/2002
EP    1378359 A1 *  1/2004 .............. B41J 2/045
(Continued)

OTHER PUBLICATIONS

John William Strutt, et al: The Theory of Sound, (Dover Publications) vol. 1, 1945, pp. 371-375.

*Primary Examiner* — Jennifer Wecker

(57) ABSTRACT

An inkjet device for controlled positioning of a droplet of a substance onto a substrate includes a print head having a nozzle configured to eject the droplet. A camera is configured to detect and generate images of the droplet after ejection of the droplet from the nozzle. If the droplet volume, velocity, flight path, viscosity or surface tension start to deviate from preset values, a computer is configured to correct for this in a closed loop manner. If the droplet fails to eject, the computer is configured to stop the inkjet device and an operator can maintain the print head. The computer is configured to determine viscosity and surface tension of the droplet from characteristics of the droplet identified from the droplet images, and the computer is configured to control the positioning of the droplet onto the substrate during the
(Continued)

printing process based on the determined viscosity and surface tension.

28 Claims, 7 Drawing Sheets

(51) Int. Cl.
    *B41J 3/54*     (2006.01)
    *B41J 2/045*     (2006.01)
    *B01L 3/02*     (2006.01)
    *C40B 50/14*     (2006.01)
    *C40B 60/14*     (2006.01)
    *G01N 35/10*     (2006.01)
    *B01J 19/00*     (2006.01)

(52) U.S. Cl.
    CPC ....... B41J 2/04508 (2013.01); B41J 2/04561 (2013.01); B41J 2/04571 (2013.01); B01J 19/0046 (2013.01); *B01J 2219/00378* (2013.01); *B01J 2219/00659* (2013.01); *B01J 2219/00689* (2013.01); *B01J 2219/00693* (2013.01); *B01L 2200/143* (2013.01); *B01L 2300/0819* (2013.01); *B01L 2400/0439* (2013.01); *G01N 35/1002* (2013.01); *G01N 2035/1041* (2013.01)

(56) References Cited

U.S. PATENT DOCUMENTS

| | | | |
|---|---|---|---|
| 6,693,292 B1 | 2/2004 | Lewis | |
| 6,705,711 B1 * | 3/2004 | Richards | B41J 2/17509 347/85 |
| 6,755,500 B2 | 6/2004 | Hirano et al. | |
| 6,877,838 B2 | 4/2005 | Elgee | |
| 6,921,636 B1 | 7/2005 | Brennan | |
| 6,925,856 B1 * | 8/2005 | Williams | G01N 11/16 73/54.41 |
| 7,300,126 B2 * | 11/2007 | Uraki et al. | 347/10 |
| 2002/0089561 A1 * | 7/2002 | Weitzel | B41J 2/125 347/19 |
| 2004/0062686 A1 * | 4/2004 | Ganz | B01J 19/0046 506/32 |
| 2004/0070641 A1 * | 4/2004 | Inoue | B41J 2/14145 347/19 |
| 2004/0082059 A1 * | 4/2004 | Webb et al. | 435/287.2 |
| 2004/0189750 A1 * | 9/2004 | Miura et al. | 347/52 |
| 2004/0196319 A1 | 10/2004 | Aruga | |
| 2004/0196329 A1 * | 10/2004 | Ready et al. | 347/40 |
| 2004/0223014 A1 | 11/2004 | Barr et al. | |
| 2004/0261700 A1 * | 12/2004 | Edwards et al. | 118/679 |
| 2004/0263550 A1 * | 12/2004 | Mitsuzawa | 347/12 |
| 2005/0104921 A1 * | 5/2005 | Watanabe | B41J 2/0456 347/19 |
| 2006/0071957 A1 * | 4/2006 | Shang et al. | 347/6 |
| 2006/0170726 A1 * | 8/2006 | Hirakawa | B41J 2/2114 347/21 |
| 2006/0210443 A1 * | 9/2006 | Stearns | B01L 3/0268 422/400 |
| 2007/0070109 A1 * | 3/2007 | White | B41J 29/393 347/19 |
| 2009/0231368 A1 * | 9/2009 | Nakano et al. | 347/8 |

FOREIGN PATENT DOCUMENTS

| | | |
|---|---|---|
| EP | 1445106 A1 | 8/2004 |
| JP | 01099859 A | 4/1989 |
| JP | 10206624 A | 8/1998 |
| JP | 11105307 A | 4/1999 |
| JP | 2003149020 A | 5/2003 |
| JP | 2004017331 A | 1/2004 |
| JP | 2004069484 A | 3/2004 |
| JP | 2004337771 A | 12/2004 |
| WO | 02098576 A1 | 12/2002 |
| WO | 03028868 A2 | 4/2003 |

\* cited by examiner

INKJET DEVICE AND METHOD FOR THE CONTROLLED POSITIONING OF DROPLETS OF A SUBSTANCE ONTO A SUBSTRATE

Inkjet device for the controlled positioning of droplets of a substance onto a substrate, method for the controlled positioning of droplets of a substance, method for determining the degeneration of the substance during the printing process and use of an inkjet device The present invention relates to an inkjet device for controlled positioning of droplets of a substance onto a substrate. The present invention further relates to a method for the controlled positioning of droplets of a substance onto a substrate using an inkjet device. The present invention further relates to a method for determining the degeneration of the substance during the printing process. The present invention further relates to the use of an inkjet device.

The present invention discloses an inkjet device for the controlled positioning of droplets of a substance onto a substrate, a method and the use of an inkjet device. Especially for diagnostics, substrates are needed where specific substances are positioned in a very precise and accurate manner. These substances are usually to be positioned on a substrate in order to perform a multitude of biochemical tests or reactions on the substrate. These substances are bio active fluids and are prone to degeneration due to enzymatic action, UV radiation, storage and the like. The inkjet device, the method for controlled positioning of droplets of a substance, the method for determining the degeneration of the substance and the use of an inkjet device according to the present invention are preferably applied to the printing process of substances onto a substrate, where the printing process has to be extremely reliable regarding the question whether a droplet of the substance has been released to the substrate, regarding the question whether a droplet of the substance has been correctly positioned on the substrate, and regarding the question whether the substance is degenerated during the printing process.

Inkjet devices are generally known. For example, US-Patent application US 2004/0196319 A1 discloses an image recording apparatus including a recording head having a plurality of nozzles, a carriage, a transfer mechanism, a driving mechanism, a detection mechanism which optically detects an injection date and a controller. The plurality of nozzles is divided into a plurality of nozzle groups. The controller times the injection of each of the nozzle groups different from that of any other nozzle group. The recording head or the plurality of recording heads according to the above cited US-Patent application can be positioned outside a printing area such that a control operation can be performed. The control operation can provide an answer to the question whether one or a plurality of printing heads or printing nozzles do not work correctly, for example because the nozzle is clogged or the like. When the printing head is positioned outside the printing area in the control or detection area, the printing heads or printing nozzles do not face the recording medium onto which the print heads apply ink droplets in the printing area. In the detection area, the trajectory of droplets intersects with a light beam detected by a photo detector leading to a control of the proper working of the printing head. A drawback of the known device is that it is not possible to answer the question whether an individual droplet has actually been positioned onto the substrate or onto the printing medium reliably because a control operation is only performed from time to time. A further drawback of the known device is that it provides no information about the possible degeneration of the substance during the printing process. This strongly limits the reliability of the printing or inkjet device especially for applications where an accurate and reliable printing process is essential.

It is therefore an object of the present invention to provide an inkjet device for the controlled positioning of droplets of a substance onto a substrate and for determining the degeneration of the substance during the printing process.

The above objective is accomplished by an inkjet device, a method for the controlled positioning of droplets of a substance, a method for determining the degeneration of the substance during the printing process according to the present invention and by the use of an inkjet device according to the present invention. The inkjet device for the controlled positioning of the droplets of a substance onto a substrate and for determining the degeneration of the substance during the printing process comprises at least a print head comprising a nozzle provided to eject a droplet, the inkjet device further comprising a control camera arranged such that after ejection of the droplet out of the nozzle, the droplet is detected by the control camera.

An advantage of the inkjet device according to the invention is that it is possible to detect the ejection of droplets out of the nozzle with very high precision by using the control camera because the control camera does not only provide a one digit binary signal like an conventional photo detector but provides an image of the droplet which has been ejected by the nozzle such that not only the presence of the droplet can be detected but preferably also the size, the velocity, the flight path of the droplet and/or the straightness of the flight path of the droplet, preferably in three dimensions.

A further advantage of the present invention is that the control camera is always directed to the outlet of the nozzle or nozzles such that any droplet or any jet of substance coming out of the nozzle can be detected. This is in contrast to detection systems of the prior art which do not have a detection means for each nozzle and which are not able to individually detect each droplet coming out of each nozzle.

A still further advantage of the present invention is that by carefully following the dynamic behaviour of the droplet, with the control camera, qualitative information can be derived about the viscosity and surface tension of the substance. It is possible to follow the extent of evaporation of the substance or the degeneration of the substrate by comparing these values of viscosity and surface tension with those measured at the beginning of the printing process.

In a preferred embodiment of the present invention, the droplet is detected while the droplet is travelling between the nozzle and the substrate. Thereby, it is possible to detect the droplet in free movement along the trajectory between the nozzle and the substrate. This means that the detection of a droplet can be made very unambiguously and undisturbed by any sources of error.

Preferably, the positioning of the droplet is continuously controlled such that each droplet is detected while travelling between the nozzle and the substrate. This has the advantage that no droplet can be left, and as such the printing process or the releasing process of droplets onto a substrate can be made even more reliable.

In a preferred embodiment of the present invention, the control camera is fixedly positioned relative to the print head. This has the advantage, that the positioning of the control camera relative to the nozzle does not change and therefore no errors due to misalignment can be induced into the detection of the droplets coming out of the nozzle.

Preferably, the control camera is mounted such that the optical axis of the control camera is inclined by an angle relative to the trajectory of the droplet. This has the advantage that it is possible to detect the droplet with a high reliability by means of the control camera. This is in particular important because space around the print head is at a premium and therefore positioning of the control camera is very important. This makes it possible to detect each ejected droplets in-line during printing, while the distance between the print head and substrate is less than 1 mm.

In a further preferred embodiment of the present invention, the inkjet device comprises at least one light source assigned to the print head. Thereby it is possible to even further improve the detection of droplets coming out of the nozzle by means of the control camera because the illumination conditions are very reliably defined by means of the light source. Preferably, the light source is provided as a stroboscope.

Preferably, the light source assigned to the print head is mounted such that light emission is orientated in the same plane and approximately orthogonal relative to the optical axis of the control camera. Thereby it is possible to realise the control mechanism of the control camera and the light source such that only little space is needed, which is important for all components moving together with the print head.

In a further preferred embodiment, the inkjet device comprises a second control camera and a second light source arranged such that after ejection of the droplet out of the nozzle, the droplet is detected by the control camera and by the second control camera. The second control camera is preferably fixed to the print head. The second camera is also mounted with an angle. From a top view, this control camera is preferably mounted with an angle of 90 degrees relative to the direction from the first control camera to the print head. This construction makes it possible to continuously monitor the droplet emission in two directions, making a 3D image of the flight path.

In a further preferred embodiment of the present invention, the inkjet device comprises a further print head, the further print head comprising a further nozzle, the inkjet device comprising a further control camera arranged such that after ejection of a further droplet out of the further nozzle, the further droplet is detected by the further control camera. Thereby, it is possible to enhance printing velocity for a given number of droplets to apply to the substrate. This reduces the production time of printed products. This is very advantageous in the case of very sensitive printed products such as bio-molecules for the use in biological assays because many sensitive compounds are involved in the production of such a cartridge and the reduction of production time reduces the risk of ageing of the substance and deterioration of the substance in general.

In a further embodiment of the present invention, the inkjet device comprises a third print head, the third print head comprising a third nozzle, the inkjet device further comprising a third control camera arranged such that after ejection of the third droplet out of the third nozzle, the third droplet is detected by the third control camera. Thereby, a further reduction of production time of the printed product is possible.

More print heads can be included according to the invention, e.g. up to about ten or twenty print heads. Furthermore, it is possible to use multi-nozzle print heads. According to the invention, it is also possible to detect if droplets are ejected by all nozzles of such a multi-nozzle print head.

It is preferred according to the present invention to use an inkjet device where the inkjet device further comprises a print table and a printing bridge, the print table being mounted moveably relative to the printing bridge along a first direction and the print head being mounted to the printing bridge such that the print head is moveable relative to the printing bridge along a second direction. Thereby it is possible to print or release droplets of a substance to a large area of application such that the production of printed products can be made quite cost effective because large substrates or individual membranes can be printed in one batch.

In a further preferred embodiment of the present invention, the inkjet device comprises at least one alignment camera for adjusting the position of the print head relative to the substrate holder. This allows the automatic and precise positioning of the print head relative to a substrate.

Further, it is preferred that the alignment camera is mounted fixedly relative to the print head or the print table. It is thereby possible to easily and quickly define an initial printing position or starting position for alignment purposes.

According to the present invention, it is preferred that the substrate is a flat substrate, a structured substrate or a porous substrate. More preferably, the substrate is a nylon membrane, nitrocellulose, or PVDF substrate. Because the substrate is preferably porous, the spots or the droplets do not only lie on the surface, but also penetrate into the membrane.

In a further embodiment of the present invention, the substrate comprises a plurality of substrate areas, each substrate area preferably being a separated membrane held by a membrane holder. Thereby, a plurality of separated membranes can be produced by the use of the inventive inkjet device.

Also preferably, the substrate comprises a plurality of substrate locations, the substrate locations being separated from each other at least the average diameter of a droplet positioned on one of the substrate locations. Thereby, it is possible to precisely and independently locate different droplets of a substance at precise locations on the substrate. It is also possible and advantageous to place a plurality of droplets on one and the same substrate location.

Preferably, the substance is a volatile solution in liquids like water, alcohols or glycerol and the like where different molecules or different compounds, especially bio-molecules are present The present invention also includes a method for the controlled positioning of droplets of a substance onto a substrate using an inkjet device comprising at least a print head comprising a nozzle provided to eject a droplet, the inkjet device further comprising a control camera arranged such that after ejection of the droplet out of the nozzle, the droplet is detected by the control camera. Preferably, the positioning of the droplet is continuously controlled such that each droplet is detected by the control camera and, also preferably, the droplet is detected while travelling between the nozzle and the substrate. Thereby a very high degree of reliability and accuracy in the printing process is possible to achieve. By using the inventive method, the droplets can be positioned at least within 25 µm or less of the predetermined position. A more precise placement of the droplets is possible by using smaller droplet volumes. This is in contrast to the graphical industry where position accuracy within a tolerance field of 40 µm is standard.

It is preferred according to the present invention that a feed back loop stops the printing process if the volume of the droplet is incorrect and/or if the velocity of the droplet is incorrect and/or if the straightness of the flight path of the droplet is incorrect or if the droplet is not being ejected from the nozzle. This has the advantage that the printing process is stopped when something goes wrong during printing (the feedback loop immediately interferes with the printing process) and that the substrate that is printed is marked (especially by software) as "incorrect" and not considered as a good product. In many cases, it cannot be determined easily afterwards if a droplet indeed has landed on the substrate, especially when the droplet is absorbed by the substrate and the solvent has been evaporated. Furthermore, software makes sure that each picture taken from a droplet is analysed and that indeed a droplet has been jetted. In a preferred embodiment, this analysis is followed by a feedback loop which stops the printer if the analysis of the ejected droplet shows that something is wrong during printing. An operator can now maintain the print head such that it operates according to the specifications and the printing process can then be resumed. In the software, the substrate which is not correctly printed is marked and removed out of the batch of printed membranes.

Preferably, the control camera is opened when a droplet is ejected from the nozzle and the light source emits a light impulse a predefined delay time after the ejection of the droplet. Directly after the flash, the camera closes and starts sending the image to the computer. This is in contrast with the standard method of visualising the droplet emission out of print heads. Standard is that the stroboscope is triggered by the droplet fire signal to the print head. By doing so an image of a number of apparently stationary droplets is made in space. As the droplet emission is a stable process it looks like one is observing just one droplet. Small disturbances make that each droplet is emitted slightly different from the previous ones causing a blurred image. This stationary image is recorded by a standard CCD camera and used for image analysis. The method using just one droplet has the advantage over the prior art that the image is built up of only one droplet. This means that the image is not blurred. This makes the calculation of the velocity, the volume and the straightness of the path of the droplet much more accurate compared to the state of the art. Furthermore, especially when using a stroboscope as the light source, there is no dependency of the light intensity at different frequencies of droplet ejection. When printing at a frequency (e.g. approximately 1000 Hz or higher) higher than the frequency (e.g. approximately 30 Hz to 200 Hz) that can be handled by the inventive device when inspecting every single droplet, not all droplets are recorded. As the droplet emission is usually very stable, it is not a problem to inspect or detect only every second or third droplet coming out of the nozzle.

Further, it is preferred that in a first step the position of the print head relative to the substrate is calibrated and in a second step the substance is positioned on the membrane. By this two-step method, it is advantageously possible to very accurately and precisely locate the droplets of the substance on the substrate or on the membrane.

In a further preferred embodiment, a plurality of different substances are applied to the substrate such that a first substance is positioned at a first substrate location and the second substance is positioned at a second substrate location. This has the advantage that by performing one and the same printing process and by only exchanging a print head or a substance reservoir to print, a multitude of different substances on the substrate can be realised which can be used in a biochemical assay cartridge.

The present invention further includes a method for determining the degeneration of droplets of a substance using an inkjet device comprising at least a print head comprising a nozzle provided to eject a droplet, the inkjet device further comprising a control camera arranged such that after ejection of the droplet out of the nozzle, the shape of the droplet is detected by the control camera. The viscosity and surface tension of the substance at the beginning of the printing process are measured. At the start of the printing process, the evolution of the droplet shape is measured with the help of the control camera. The shape of the droplet changes as a function of time. Upon leaving the nozzle it starts as a long slender jet. The surface tension of the substance then drives the long slender jet to a spherical drop. The evolution of the shape of the droplet in time is a damped harmonic oscillation with a characteristic periodic time. From the periodic time and the radius of the droplet, the surface tension can be calculated using Rayleigh's formula. The damping or time it takes for the droplet to reach a stable spherical shape depends on the viscosity. The higher the viscosity the shorter the time interval needed for the droplet to arrive at the stable spherical shape. During printing the damping and the periodic time are measured either continuously or from time to time. Changes in the periodic time can be attributed to changes in the surface tension; changes in the rate of damping can be attributed directly to changes in viscosity. These values of surface tension and viscosity of the substance should be substantially close to the initial values measured before filling the print head.

It is preferred according to the present invention that a feed back loop stops the printing process when the changes in surface tension and damping (viscosity) are not within a certain tolerance band. When changes become too large the process must be stopped followed by a thorough cleaning of the print head and refilling it with a freshly prepared substance. When the viscosity and surface tension as measured with the method proposed stay within 10% of the initial values, the printing process continues. On the other hand, when deviations larger than 10% are detected the feedback loop stops the printing process The present invention also includes the use of an inventive inkjet device according to the present invention, wherein the substance comprises a biochemical reactant and/or a nucleic acid and/or a polypeptide and/or a protein. By using the inventive inkjet device for such a purpose, it is possible to very accurately and precisely locate a certain number of substances on a substrate.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

FIG. 1 illustrates schematically a top view of an embodiment of the inkjet device of the present invention, FIG. 2 illustrates schematically a cross section of a substrate area and a membrane holder, FIG. 3 illustrates schematically a cross section of the print head positioned above a substrate area and a membrane holder together with a control camera, FIG. 4 illustrates schematically the positioning of an alignment camera relative to the substrate and the print head, FIGS. 5a and 5b illustrate schematically a part of a substrate area together with a membrane holder and a complete membrane, FIG. 6 illustrates schematically an embodiment of an inkjet device of the present invention comprising a plurality of print heads, FIG. 7 illustrates schematically the inkjet device of the present invention in an inspection position, FIG. 8 illustrates schematically an embodiment of the inkjet device of the present invention with a control camera and a second control camera assigned to one print head;

Figure 1:
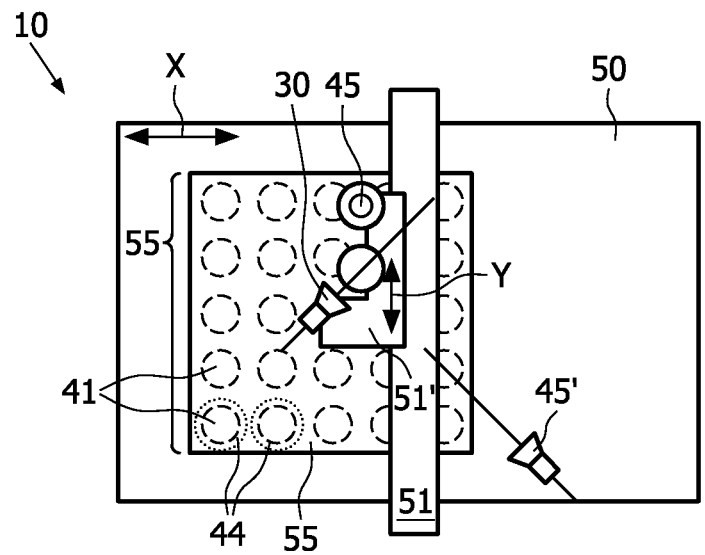

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operating in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In FIG. 1, a schematic top view of the inkjet device 10 according to the present invention is shown. On a print table 50 (preferably made of heavy granite) a fixture plate 55 is mounted fixedly on a linear stage allowing for motions in the X direction. In this fixture plate 55, a number of membrane holders 44 with membranes 41 are positioned. The membranes 41 together form the substrate. Therefore, the membranes 41 could also be called "substrate". For the sake of clarity, in the following, the term "substrate" refers to the totality of the printable area of the "membranes 41". The membrane holder 44 is basically only a ring 44. A round membrane 41 is welded onto this ring. So, after printing, the ring 44 with spotted membrane 41 together is the final product. A printing bridge 51 is provided moveably relative to the fixture plate 55 and rigidly mounted relative to the print table 50 (preferably a heavy granite table). The printing bridge 51 carries the movable print head holder 51'. The stage with the fixture plate 55 is moveable along a first direction, the X-direction. A print head is mounted onto the movable print head holder 51' such that it is moveably along a second direction, the Y-direction, relative to the printing bridge 51. According to the present invention, it is preferred that the first direction (X-direction) and the second direction (Y-direction) are orthogonal. Thereby, the print head can be moved over a certain area of a print table 50 and can release droplets of a substance which is stored in a reservoir (not shown) near the print head. The membranes 41 are mounted in the fixture plate 55, also called registration plate 55 at uniform distance in X-direction and uniform distance in Y-direction. The distance in X-direction may differ from the distance in Y-direction. According to the present invention, a control camera 30 is provided such that a droplet (shown in FIG. 3, item 22) of a substance being ejected from a nozzle of the print head can be detected by the control camera 30. In a preferred embodiment of the present invention shown in FIG. 1, the control camera 30 is fixedly positioned near the print head on the movable print head holder 51'.

The substrate may be made of a bio active membrane used for the detection of infectious diseases. Diagnostics of such diseases demand for a very high reliability of the printing process. The read out of the fluorescent pattern relates diseases directly to the positions of the specific capture probes. Therefore, it is absolutely necessary to have a very reliable process for the correct positioning of the capture probes on the substrate. Inkjet printing is a precision dosing technique without any feedback about the actual presence and placements of the droplets on the substrate. The problem is that there is no information about a course of the process. The present invention describes an optical method to follow instantaneously the printing process of each print head. On the inkjet device 10, two microscopes are mounted equipped with CCD cameras that measure both the landing position of the droplet and continuously monitor the printing process. At the very moment a droplet is missing or lands outside the predefined landing position (substrate locations 42), the system stops the printing process and marks the just printed membrane 41 or substrate area. The operator can now maintain the print head (pipette) such that it operates according to the specification and the printing process can be resumed. Later on, the marked membrane can be removed out of the batch of printed membranes 41.

The print table 50 is preferably provided in the form of a granite table. Alternatively, another very heavy material can be used. According to the present invention, the print table 50 should be arranged in an environment which has very little vibrational disturbances. A precision linear stage is mounted relative to the granite table (print table 50) and a fixture plate 55 mounted on the stage moves by definition in the first direction (X-direction).

Figure 7:
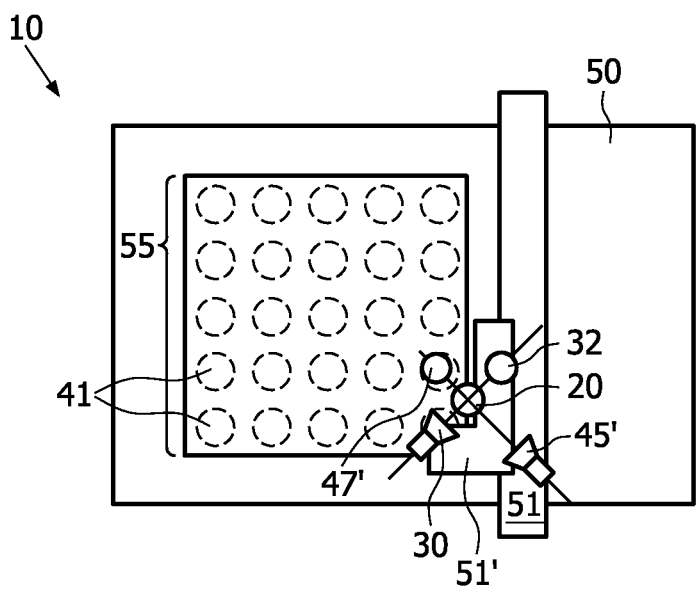

In the embodiment shown in FIG. 1, an alignment camera 45 is also positioned near the print head. The alignment camera 45 is positioned at a defined distance from the print head. By viewing a certain structure on the fixture plate 55 or on the substrate, it is possible to calibrate or to position the print head relative to the print table 50 and therefore relative to the membranes 41. An inspection camera 45' (with an inspection light source 47' shown in FIG. 7) is positioned fixedly relative to the print table 50. By moving the print head to an inspection position, as represented in FIG. 7, the two cameras (control camera 30 and the inspection camera 45') are positioned with an angle of 90 degrees respectively to each other. This makes it possible to measure in two dimensions the droplet volume, droplet velocity and droplet flight path. These data can be stored and transferred to the computer controlling the printing program. By correcting for the deviations in the flight path, it can be assured that the droplet always lands on the predetermined position.

The control camera 30 and the inspection camera 45' are basically the same and used for the same purpose. The only difference between control camera 30 and inspection camera 45' is that control camera 30 is used during the whole printing process, while inspection camera 45' is used only during inspection prior to printing. Alignment camera 45 is different as this one is only used before printing a complete batch to align the fixture plate 55 to the print table 50.

Figure 2:
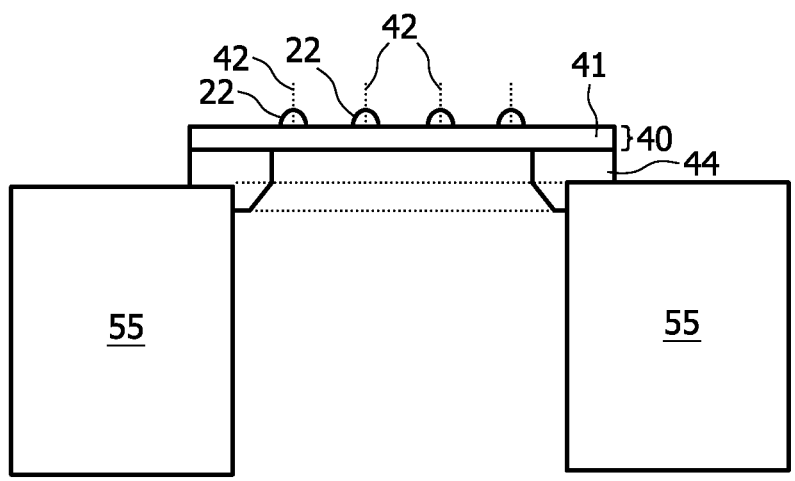

In FIG. 2, a schematic representation of a cross sectional view of an individual substrate membrane holder 44 and a part of the fixture plate 55 is shown. The membrane holder 44 carries one membrane 41 as part of the substrate 40. One membrane 41 is also called a substrate area 41. Each individual membrane holder 44 is located on the fixture plate 55 fixedly mounted on a linear stage allowing for a linear motion in the X-direction relative to the granite table (print table) 50. On the substrate 40, i.e. on each membrane 41, a plurality of substrate locations 42 are provided at a distance from one another such that an individual droplet (schematically shown by reference sign 22 in FIG. 2) is able to be located at. Thereby, it is possible to dispense or to position a different kind of substance on each of the substrate locations 42.

Figure 3:
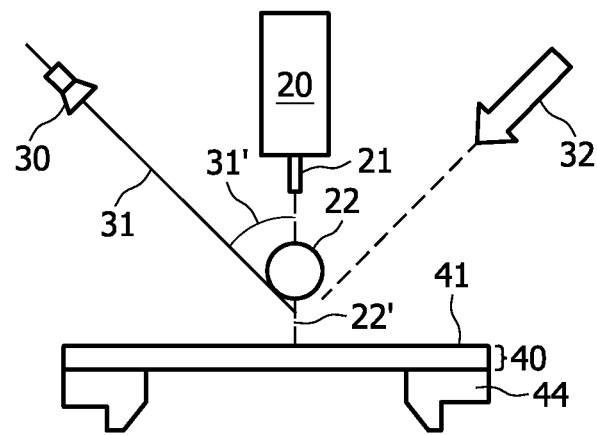

In FIG. 3, a schematic cross sectional representation of the arrangement of the control camera 30 of the inventive inkjet device 10 is shown. On the membrane holder 44, the membrane 41 or the substrate area 41 is located. The print head 20 comprises the nozzle 21 being able to eject a droplet 22. The droplet 22 moves from the nozzle 21 towards the surface of the substrate 40 on a trajectory 22'. During this trajectory 22', the control camera 30 is able to view an image of the droplet 22 travelling from the nozzle 21 towards the surface of the substrate 40. For the control camera 30 to be able to see the droplet 22, a light source 32 (preferably a stroboscope or controllable flash light) is positioned in an angle to the optical axis 31 of the control camera 30. The arrangement of the camera is such that the angle with respect to the surface of the substrate 40 is as small as possible allowing for an as large as possible field of view under the nozzle 21. The same holds true for the optical axis of the stroboscopic illumination system. The droplet 22 is preferably illuminated indirectly by reflection via the substrate 40. According to an embodiment of the present invention, the optical axis of the control camera 30 is inclined by an angle. The light source 32 is preferably mounted fixedly relative to the print head 20.

Figure 4:
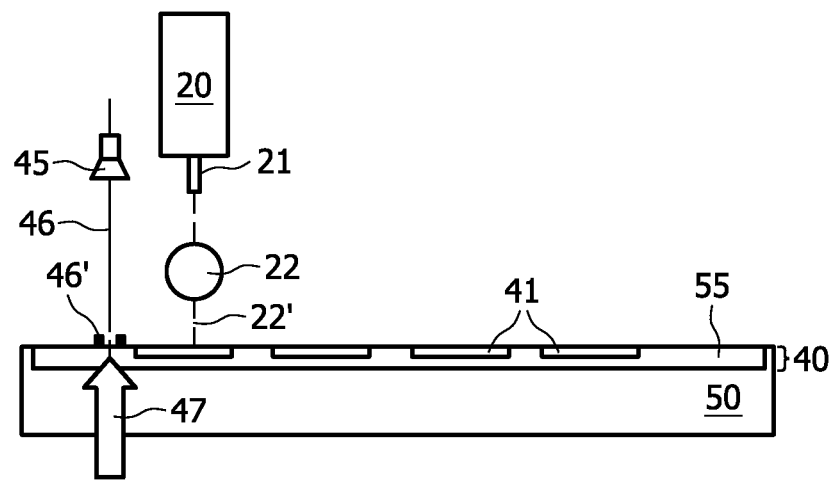

In FIG. 4, a schematic representation of the alignment step of the print head 20 relative to the membrane 40 or relative to the print table 50 is shown. The alignment camera 45 is positioned (e.g. vertically) such that a structure 46' on the print table 50 or on the fixture plate 55 is visible by the alignment camera 45 if the print head 20 and the printing bridge 51 are positioned accordingly. A further source of light 47 is positioned preferably such that the structure 46' is clearly visible by the alignment camera 45. Therefore, the further light source 47 is approximately aligned with the optical axis 46 of the calibration camera 45.

Figure 5A:
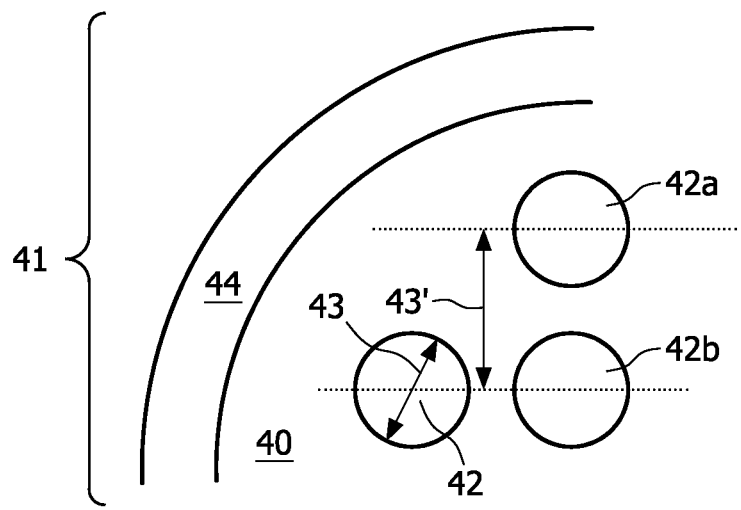

In FIG. 5a, a part of a membrane 41 or a substrate area 41 is shown from the top. On the substrate area 41 are defined a plurality of substrate locations 42, 42a, 42b. The substrate locations 42, 42a, 42b are the locations where the droplets 22 are to be positioned by the inkjet device 10 according to the present invention. It is also possible to place a plurality of droplets on one single substrate location 42. The droplets 22 which have been ejected by the print head 20 and landed on the substrate 40 will cover a certain droplet area or spot around the substrate locations 42, 42a, 42b with an average diameter 43 which is lower than the respective distance 43' (or pitch) of the substrate locations 42, 42a, 42b from one another.

Figure 5B:
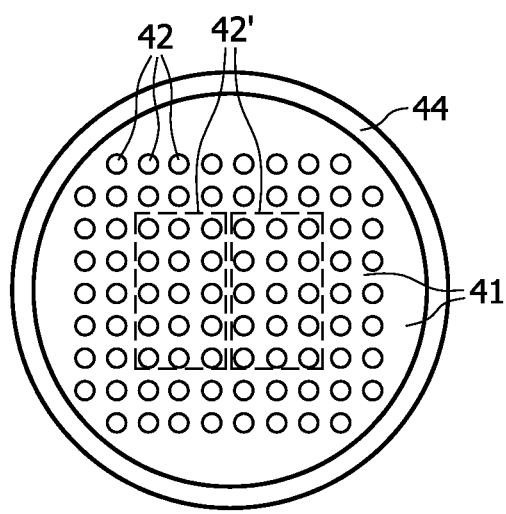

In FIG. 5b a top view of a substrate area 41 is shown where a plurality of substrate locations 42 are represented by small circles. According to the present invention, many different substances can be positioned on these different substrate locations 42 in order to use the membrane of the substrate area 41 for diagnostic purposes. According to the present invention, it is possible to define several groups 42' of substrate locations 42 in order to perform a complete set of tests within one group 42' of substrate locations 42 and their respective substances.

Figure 6:
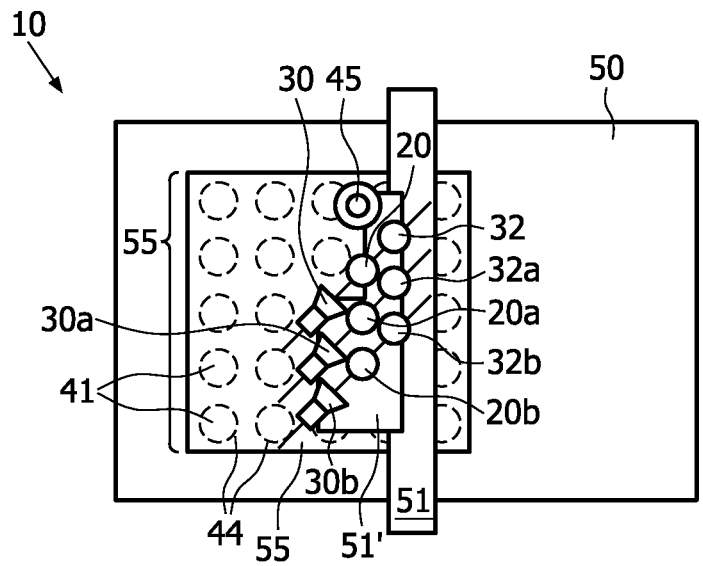

In FIG. 6, a further embodiment of the inkjet device 10 of the present invention is schematically and partly shown. The printing bridge 51 is provided with a further print head 20a and third print head 20b in addition to the print head 20. Accordingly, a further control camera 30a and third control camera 30b are positioned near the print heads 20, 20a and 20b. According to the present invention, it is preferable to provide as well a further light source 32a assigned to the further control camera 30a and a third light source 32b assigned to the third control camera 30b.

In the embodiment according to FIG. 6, up to three or more single nozzle print heads 20, 20a, 20b mounted rigidly on the linear stage on the bridge 51 move by definition in the second direction (Y-direction). The print heads 20, 20a, 20b can be moved to any position on the substrate by simultaneously moving the substrate along the X-direction and/or the printing bridge 51 together with the print heads 20, 20a, 20b along the Y-direction. The distance of the print heads 20, 20a, 20b is as close as possible to the distance of the membranes 41 in Y-direction. The print heads 20, 20a, 20b can be filled with the same fluid or each with a different fluid. By the use of more than one print head 20, a decrease in print time can be obtained when a number of single nozzle print heads are used in parallel.

Figure 8:
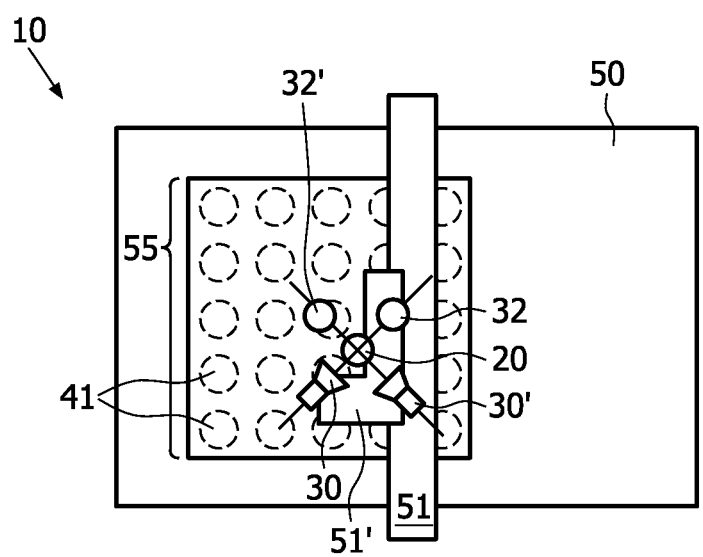

In FIG. 8, a further embodiment of the inkjet device 10 is shown. In this embodiment and in contrast to the embodiment shown in FIGS. 1 and 7, a second control camera 30' is also (like the control camera 30) mounted rigidly onto the print head.

In FIGS. 1-7, only during inspection the flight path of the droplets can be recorded in both directions. During printing, only control camera 30 records images of droplets 22.

In the embodiment as shown in FIG. 8, during inspection as well as during printing, images of droplets 22 in both directions are obtained.

According to the invention, the print protocol is processed preferably in the following manner: Preferably, the membranes 41 are firstly aligned by means of the alignment camera 45 and the structure 46'. Then, a first fluid of a substance is put into the print head 20. The print table 50 moves to the inspection position (FIG. 7). While at this inspection position, two cameras (control camera 30 and inspection camera 45') are positioned under an angle of 90° with each other, thus making it possible to see droplets 22 in both directions. By doing this, it can be ensured that the position information of the droplet 22 is known in three dimensions and not only in two dimensions as would be the case when a single camera is used. At the inspection position, both cameras measure preferably the volume, the velocity and the straightness of the droplet. This is all recorded by software and stored in a memory. The deviation of the ideal flight path of the droplet is calculated in both directions and this deviation is automatically corrected for in the software. This makes it possible to position the droplets automatically. Thereafter, the fixture plate 55/print head 20 starts moving to the membranes 41.

In one embodiment (FIGS. 1 and 7), only one camera (control camera 30 assigned to the print head) moves together with the print head 20 and records all droplets one by one. The software performs an analysis of the images recorded. In case anything goes wrong (e.g. wrong flight path, wrong volume of the droplets 22, no droplet at all), the software interferes with the printing process and the printing is stopped. The membrane 41 at which the failure took place is marked in the software such that this product (membrane 41 with membrane holder 44) is not sold. After maintaining the print head 20, the printing process can be resumed where it stopped.

In another embodiment (FIG. 8), two cameras (control camera 30 and second control camera 30') are fixed to the print head 20 and both cameras record images of each droplet 22. In this embodiment, extra precaution is taken to be sure that in case anything goes wrong in three dimensions, it is recorded. In case anything goes wrong (e.g. wrong flight path, wrong volume of the droplets 22, and no droplet at all), the software interferes with the printing process and the printing is stopped. The membrane 41 at which the failure took place, is marked in the software such that this product (membrane 41 with membrane holder 44) is not sold. After maintaining the print head 20, the printing process can be resumed where it stopped.

On a substrate area 41, for example 130 spots or substrate locations 42 can be provided where droplets 22 can be printed, each droplet needing a volume of, e.g., around 1 nl. The diameter 43 of the spots or the droplets 22 is for example 200 μm and they are placed in a pattern with a pitch of, e.g., 400 μm. Of course, it is also possible to provide smaller spots necessitating only a smaller pitch of, for example, 300 μm or only 200 μm, 100 μm or 50 μm. The 130 spots are printed for example with one single print head 20 which is provided with different substances 23. For example, on the fixture plate 55, 140 pieces of membrane holders 44 are arranged which are processed in one batch of printing by the inkjet device 10. The pitch 43' of the droplet spots is provided in the range of 10 to 500 μm according to the present invention. The diameter 43 of the spots of the droplets 22 is in the range of about 20% to 70% of the actual pitch 43'. The volume of the droplets 22 has to be adapted to the preferred size of the spot and to the material of the substrate 40 used (e.g. dependent of where the substrate strongly or weakly absorbs the substance applied). Typically, the volume of the droplets 22 is about 0,001 nl to 10 nl.

Figure 9:
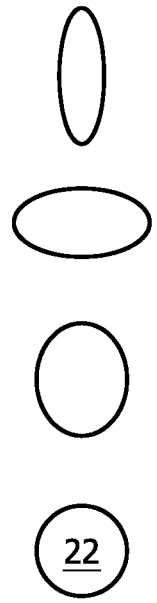
FIG. 9 illustrates schematically a stroboscopic image of droplet formation of a substance with viscosity of around 1 mPas.
Figure 10:
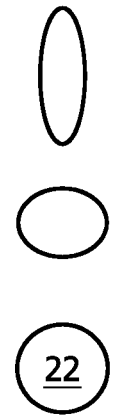
FIG. 10 illustrates schematically a stroboscopic image of droplet formation of a substance with viscosity of around 5 mPas.

In FIGS. 9 and 10, the stroboscopic images of evolution of a droplet 22 of a substance 23 are shown. A droplet in equilibrium is a perfect sphere with radius R. The invention is based on the observation that when a droplet 22 leaves the nozzle 21 of a print head it is initially strongly distorted. The surface tension of the droplet 22 attempts to smooth the distortion by trying to make the droplet 22 spherical. This smoothening of the shape of the distorted droplet 22 causes the substance 23 in the distorted droplet 22 to accelerate; at the moment the droplet 22 is about spherical the internal velocity distribution in the droplet 22 is maximal, causing the droplet 22 to become ellipsoidal again. The motion of the substance 23 in the droplet 22 is decelerated by the action of surface tension. This action strongly resembles the behaviour of a mass-spring system. The mass is the mass of the substance in the droplet; the spring is the action of surface tension. J. W. Strutt, Lord Rayleigh in his treatise on "The Theory of Sound" (Dover Publications 1945, pp 371-375) has derived an expression for the basic frequency (key tone) of free vibrating droplet:

$$f = \sqrt{\frac{8\sigma}{4\pi^2 \rho R^3}} \quad (1)$$

Where f is the key tone frequency, σ is the surface tension, ρ is the density and R is the radius of the droplet. To place this formula in perspective let us assume the vibrations of a droplet of 100 pl (R=28.8 μm) of water with a density of 1000 kg/m3 and a surface tension of 0.07 N/m. The basic frequency equals 24.37 kHz. The periodic time is 41 μsec. A droplet leaving the nozzle with a speed of 3 m/s shows a complete vibration over a flying distance of 123 μm, a value easily observable by standard optical means. In case the surface tension is lowered by a surface active agent to say 0.035 N/m the frequency becomes 12.18 kHz, the periodic time 82 μsec and the flight path covered by one vibration 250 μm. The viscosity damps the vibration and the higher the viscosity the stronger the damping.

Figure 11:
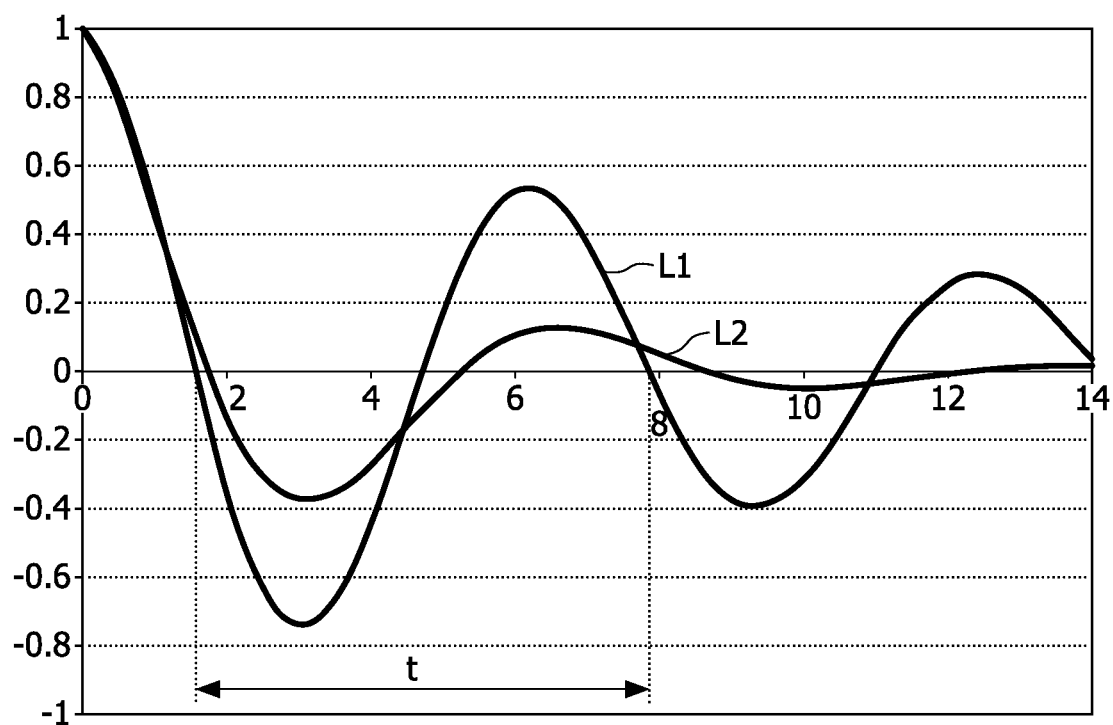
FIG. 11 illustrates the deviations from spherical shape of a droplet as a function of time.

FIG. 11 shows the deviations from the spherical shape of a droplet 22 as a function of time. L1 shows the deviations for a freshly prepared substance and L2 shows the deviations for a slightly dried substance. Both x and y axes are in arbitrary units. 't' is the periodic time. From FIG. 11, periodic time is calculated. Reciprocal of periodic time is frequency. Equation (1) gives the relation between frequency and surface tension. With the known values of radius and density, surface tension can be calculated. The damping or time it takes for the droplet to reach a stable spherical shape depends on the viscosity. The higher the viscosity the shorter the time interval needed for the droplet to arrive at the stable spherical shape. During printing the damping and the periodic time are measured either continuously or from time to time. Changes in the periodic time can be attributed to changes in the surface tension; changes in the rate of damping can be attributed directly to changes in viscosity.

The invention claimed is:

1. An inkjet device for the controlled positioning of a droplet of a substance onto a substrate and for determining degeneration of the substance during a printing process, the inkjet device comprising:
    a first print head comprising a first nozzle configured to eject the droplet;
    a first camera configured to generate images of the droplet as the droplet travels between the first nozzle and the substrate; and
    a computer configured to determine a determined viscosity and a determined surface tension of the droplet from characteristics of the droplet identified from the images of the droplet,
    wherein the computer is further configured to control positioning of the droplet of the substance onto the substrate during the printing process in accordance with the determined viscosity and the determined surface tension.

2. The inkjet device according to claim 1, wherein the first camera is configured to detect each droplet ejected from the first nozzle and to generate images of each droplet ejected while each droplet is travelling between the first nozzle and the substrate.

3. The inkjet device according to claim 1, wherein the computer is configured to measure volume, velocity, and straightness of the droplet.

4. The inkjet device according to claim 1, wherein the first camera is fixedly positioned relative to the first print head.

5. An inkjet device for controlled positioning of a droplet of a substance onto a substrate and for determining degeneration of the substance during a printing process, the inkjet device comprising:
  a first print head comprising a first nozzle configured to eject the droplet; and
  a first camera configured to generate images of the droplet as the droplet travels between the first nozzle and the substrate,
  wherein the first camera is mounted such that an optical axis of the first camera is inclined by an angle different than 90 degrees relative to a trajectory of the droplet travelling between the first nozzle and the substrate.

6. The inkjet device according to claim 1, further comprising a light source assigned to the first print head.

7. The inkjet device according to claim 6, wherein the light source is mounted such that light emission is oriented approximately orthogonal relative to an optical axis of the first camera.

8. The inkjet device according to claim 5, further comprising a second camera configured, such that after ejection of the droplet out of the first nozzle, the droplet is detected by the first camera and by the second camera,
  wherein the second camera is mounted with an angle of 90 degrees relative to a direction from the first camera to the first print head.

9. The inkjet device according to claim 1, wherein the inkjet device comprises a multi nozzle print head.

10. The inkjet device according to claim 1, further comprising:
  a second print head including a second nozzle; and
  a second camera configured to detect a droplet ejected out of the second nozzle after ejection of the droplet out of the second nozzle.

11. The inkjet device according to claim 10, further comprising:
  a third print head, the third print head comprising a third nozzle; and
  a third camera configured to detect a droplet ejected by the third nozzle.

12. The inkjet device according to claim 1, further comprising:
  a print table,
  and a printing bridge; and
  a stage with a fixture plate configured to move relative to the print table along a first direction, wherein the first print head is mounted on a movable print head holder that is mounted onto the printing bridge such that the first print head is configured to move relative to the printing bridge along a second direction.

13. The inkjet device according to claim 12, wherein the first direction and the second direction are orthogonal.

14. The inkjet device according to claim 8, wherein the inkjet device further comprises an alignment camera configured to provide information for aligning a position of the first print head relative to a print table and a movable substrate holder.

15. The inkjet device according to claim 14, wherein the alignment camera is mounted fixedly relative to one of the first print head and the print table.

16. The inkjet device according to claim 1, wherein the substrate is one of a flat substrate, a structured substrate, a porous membrane, and a nylon membrane.

17. The inkjet device according to claim 1, wherein the substrate comprises a plurality of substrate areas, each substrate area being a separated membrane held by a membrane holder.

18. The inkjet device according to claim 1, wherein the substrate comprises a plurality of substrate locations, the substrate locations being separated from each other by at least an average diameter of the droplet positioned at one of the substrate locations.

19. The inkjet device of claim 1, wherein the computer is configured to compare the determined surface tension and the determined viscosity of a first droplet with the determined surface tension and the determined viscosity of a second droplet, and wherein the computer is configured to discontinue ejection of droplets through the first nozzle when differences between the compared surface tensions and viscosities exceed predetermined thresholds.

20. An inkjet device for controlled positioning of a droplet of a substance onto a substrate and for determining degeneration of the substance during a printing process, the inkjet device comprising:
  a first print head comprising a first nozzle configured to eject the droplet;
  a first camera configured to generate images of the droplet as the droplet travels between the first nozzle and the substrate; and
  a computer configured to determine a viscosity and a surface tension of the droplet from characteristics of the droplet identified from the images of the droplet,
  wherein the computer is further configured to control the printing process in accordance with the viscosity and the surface tension determined by the computer,
  wherein:
  the surface tension of the droplet is determined from a radius of the droplet identified within the images of the droplet and a density of the substance,
  the viscosity of the droplet is determined from an amount of time the droplet requires to reach a stable spherical shape within the images of the droplet, and
  the stable spherical shape is one within predetermined deviations from a perfectly spherical shape.

21. The inkjet device of claim 20, wherein the amount of time for the droplet to reach the stable spherical shape is calculated from a relation:

$$t = \left( \sqrt{\frac{8\sigma}{4\pi^2 \rho R^3}} \right)^{-1}$$

where t is the amount of time, σ is the surface tension of the droplet, ρ is the density of the droplet, and R is the radius of the droplet.

22. The inkjet device of claim 1, wherein the computer is configured to determine a volume of the droplet from the images of the droplet, and is further configured to prevent the first print head from ejecting a subsequent droplet through the first nozzle when the determined volume is not within a predetermined range.

23. A method executed by an inkjet device for controlled positioning of a droplet of a substance onto a substrate and for determining degeneration of the substance during a printing process, the method comprising acts of:
ejecting the droplet from a nozzle of a print head;
generating, with a camera, images of the droplet as the droplet travels between the nozzle and the substrate;
determining, with a computer, a determined viscosity and a determined surface tension of the droplet from characteristics of the droplet identified from the images of the droplet; and
controlling, with the computer, positioning of the droplet of the substance onto the substrate during the printing process in accordance with the determined viscosity and the determined surface tension.

24. The method of claim 23, further comprising acts of:
comparing, with the computer, the determined surface tension and the determined viscosity of a first droplet with the determined surface tension and the determined viscosity of a second droplet; and
discontinuing the act of ejecting of the droplet from the nozzle when differences between the compared surface tensions and viscosities exceed predetermined thresholds.

25. A method executed by an inkjet device for controlled positioning of a droplet of a substance onto a substrate and for determining degeneration of the substance during a printing process, the method comprising acts of:
ejecting the droplet from a nozzle of a print head;
generating, with a camera, images the droplet as the droplet travels between the nozzle and the substrate;
determining, with a computer, a viscosity and a surface tension of the droplet from characteristics of the droplet identified from the images of the droplet; and
controlling, with the computer, the printing process in accordance with the viscosity and the surface tension determined with the computer,
wherein the determining act comprises acts of:
determining, with the computer, a radius of the droplet identified within the images of the droplet and a density of the substance for the determining of the surface tension of the droplet, and
determining, with the computer, an amount of time the droplet requires to reach a stable spherical shape within the images of the droplet for the determining of the viscosity of the droplet, wherein the stable spherical shape is one within predetermined deviations from a perfectly spherical shape.

26. The inkjet device of claim 25, wherein the amount of time for the droplet to reach the stable spherical shape is calculated from a relation:

$$t = \left( \sqrt{\frac{8\sigma}{4\pi^2 \rho R^3}} \right)^{-1}$$

where t is the amount of time, σ is the surface tension of the droplet, ρ is the density of the droplet, and R is the radius of the droplet.

27. The inkjet device according to claim 5, further comprising a second camera configured, such that after ejection of the droplet out of the first nozzle, the droplet is detected by the first camera and by the second camera,
wherein the first camera and the second camera are configured to continuously monitor the droplet ejected from the first nozzle in two directions, and
wherein the first camera and the second camera are configured to generate a 3-dimensional image of a flight path of the droplet as the droplet travels between the first nozzle and the substrate.

28. The inkjet device according to claim 6, wherein the light source is configured to emit a light impulse a predefined delay time after ejection of the droplet from the first nozzle.

* * * * *